United States Patent
Reinold et al.

(10) Patent No.: US 9,573,893 B2
(45) Date of Patent: Feb. 21, 2017

(54) METHOD FOR PRODUCING EQUILIBRIUM PERACETIC ACID AND EQUILIBRIUM PERACETIC ACID OBTAINABLE BY THE METHOD

(71) Applicant: EVONIK DEGUSSA GMBH, Essen (DE)

(72) Inventors: Andreas Reinold, Gründau (DE); Stefan Leininger, Langenselbold (DE); Angela Hellwig, Dreieich (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/440,182

(22) PCT Filed: Oct. 9, 2013

(86) PCT No.: PCT/EP2013/071013
§ 371 (c)(1),
(2) Date: May 1, 2015

(87) PCT Pub. No.: WO2014/072143
PCT Pub. Date: May 15, 2014

(65) Prior Publication Data
US 2015/0291520 A1    Oct. 15, 2015

(30) Foreign Application Priority Data
Nov. 8, 2012  (EP) ..................... 12191799

(51) Int. Cl.
*C07C 409/26* (2006.01)
*C07C 7/00* (2006.01)
*C07C 407/00* (2006.01)

(52) U.S. Cl.
CPC ........... *C07C 409/26* (2013.01); *C07C 407/00* (2013.01)

(58) Field of Classification Search
CPC ... C07C 409/24; C07C 407/26; C07C 407/003
USPC ............................................................. 562/6
See application file for complete search history.

(56) References Cited

U.S. PATENT DOCUMENTS

| | | | |
|---|---|---|---|
| 3,360,531 A | | 12/1967 | French |
| 3,625,975 A | * | 12/1971 | Crampton ............. C07C 409/24 549/272 |
| 4,115,410 A | * | 9/1978 | Watts ................... C07D 301/14 549/525 |
| 4,587,264 A | | 5/1986 | Jourdan-Laforte et al. |
| 5,767,308 A | | 6/1998 | Thiele et al. |
| 2002/0177732 A1 | * | 11/2002 | Pohjanvesi et al. .............. 562/6 |

FOREIGN PATENT DOCUMENTS

| | | |
|---|---|---|
| CN | 1070639 A | 4/1993 |
| CN | 1803771 A | 7/2006 |
| EP | 0742206 A1 | 11/1996 |
| EP | 1004576 A1 * | 5/2000 |
| JP | 52-18197 B1 | 5/1977 |
| WO | WO-01/29004 A1 | 4/2001 |
| WO | WO-03/051843 A1 | 6/2003 |

OTHER PUBLICATIONS

Itoi, Yasushi, Preparation of peroxycarboxylic acids, JP 10330357 abstract, Dec. 1998.*
Le Rouzic et al., EP 1226835 Abstract, Jul. 2002.*

* cited by examiner

*Primary Examiner* — Jafar Parsa
(74) *Attorney, Agent, or Firm* — Reed Smith LLP; Eric J. Evain; Ryan P. Cox

(57) ABSTRACT

The invention relates to a method for producing equilibrium peracetic acid by reacting acetic acid with hydrogen peroxide in an aqueous reaction mixture in the presence of methanesulphonic acid as catalyst, and also to the equilibrium peracetic acid obtainable by the method.

10 Claims, No Drawings

METHOD FOR PRODUCING EQUILIBRIUM PERACETIC ACID AND EQUILIBRIUM PERACETIC ACID OBTAINABLE BY THE METHOD

CROSS REFERENCE TO RELATED APPLICATIONS

This application is a National Phase filing under 35 U.S.C. §371 of PCT/EP2013/071013 filed on Oct. 9, 2013; and this application claims priority to application Ser. No. 12/191,799.1 filed in Europe on Nov. 8, 2012 under 35 U.S.C. §119. The entire contents of each application are hereby incorporated by reference.

The invention relates to a method for producing equilibrium peracetic acid and the equilibrium peracetic acid of low corrosivity obtainable by the method.

Peroxyacetic acid is used as a disinfectant which shows broad activity against bacteria and other microorganisms, as well as viruses, even at low temperatures, and against which bacteria and viruses do not develop resistance. Here, peroxyacetic acid has the advantage that, at the use concentrations which are used for disinfection, complete hydrolysis to acetic acid and hydrogen peroxide occurs after some time, so that the biocidal activity is lost and an accumulation of biocide cannot occur.

Peroxyacetic acid is usually put on the market in the form of equilibrium peracetic acid which, for the application, is brought to the desired use concentration with water. Equilibrium peracetic acid here denotes a mixture containing peroxyacetic acid, hydrogen peroxide, acetic acid and water in chemical equilibrium. The chemical equilibrium is thereby established between these four components according to the following reaction equation:

$$CH_3C(O)OH + H_2O_2 \rightleftharpoons CH_3C(O)OOH + H_2O$$

Equilibrium peracetic acid is usually produced from acetic acid and aqueous hydrogen peroxide solution by establishing this equilibrium. However, in the absence of further components, establishing the equilibrium takes place slowly and requires several days at 20° C. Therefore, sulphuric acid is usually added as catalyst to accelerate establishing the equilibrium. In disinfection applications, an addition of relatively large amounts of sulphuric acid also permits to control the metered amount of peroxyacetic acid via the conductivity of the disinfection solution.

Equilibrium peracetic acid containing sulphuric acid has the disadvantage that it acts corrosively on metal materials and that it cannot be stored in contact with stainless steel, since iron ions dissolved from the material catalyse the decomposition of peroxyacetic acid.

EP 0 087 343 proposes to use nitric acid as a catalyst for producing equilibrium peracetic acid. Although pitting corrosion on stainless steel may be reduced thereby, so many iron ions are still dissolved from stainless steel by such equilibrium peracetic acid that the equilibrium peracetic acid is not storage-stable in contact with stainless steel.

EP 0 742 206 A1 proposes to use polyphosphoric acid as a catalyst for producing equilibrium peracetic acid. An equilibrium peracetic acid is obtained by addition of 0.2 to 10% by weight polyphosphoric acid which is storage-stable in the presence of stainless steel. However, it is disadvantageous that polyphosphoric acid is highly viscous and therefore difficult to meter in the production of equilibrium peracetic acid. Furthermore, in the treatment of large water volumes, such as the disinfection of sewage treatment effluents or treatment of ballast water of ocean-going vessels, the content of polyphosphoric acid can lead to an unwanted eutrophication of bodies of water.

Therefore, there is still a need for a method for producing equilibrium peracetic acid by reaction of acetic acid with hydrogen peroxide which does not have the disadvantage of the method known from EP 0 742 206 A1 and provides an equilibrium peracetic acid which is storage-stable in the presence of stainless steel and does not have eutrophicating activity.

JP 10-330357 describes a production of peroxyacetic acid by reacting butyl acetate with 60% by weight hydrogen peroxide solution, with addition of methanesulphonic acid as catalyst. Corrosion problems are to be avoided by reaction in the absence of a carboxylic acid.

Utility model DE 20 2007 005 732 U1 describes a cleaning agent for removing solid deposits in drinking water conduits, which cleaning agent contains 1 to 14% by weight amidosulphonic acid, 5 to 10% by weight methanesulphonic acid, 0.075 to 0.15% by weight phosphonobutanetricarboxylic acid, 0.3% by weight 2-propanol and water to make 100%. The cleaning agent can be given a disinfecting activity by adding 1 to 10% by weight disinfectant, where hydrogen peroxide-containing substances, such as, e.g., peracetic acid, can be used as disinfectant.

WO 2012/001276 describes compositions for the dissolution of oxalate deposits, which compositions contain methanesulphonic acid and additionally phosphoric acid or nitric acid. The compositions may contain one or more additives and bromoacetic acid, peracetic acid, salicylic acid and hydrogen peroxide are mentioned, inter alia, as disinfectant.

It has now surprisingly been found that the abovementioned problems can be solved if methanesulphonic acid is used as catalyst for the production of equilibrium peracetic acid from acetic acid and hydrogen peroxide.

The invention therefore relates to a method for producing equilibrium peracetic acid by reacting acetic acid with hydrogen peroxide in an aqueous reaction mixture, wherein the reaction is carried out in the presence of methanesulphonic acid as catalyst.

The invention also relates to the use of methanesulphonic acid as catalyst for producing equilibrium peracetic acid from acetic acid and hydroxide peroxide.

The invention further relates to an equilibrium peracetic acid which comprises peroxyacetic acid, hydrogen peroxide, acetic acid and water, and contains methanesulphonic acid.

In the method according to the invention, acetic acid and hydrogen peroxide are reacted in an aqueous reaction mixture in the presence of methanesulphonic acid to form equilibrium peracetic acid. Methanesulphonic acid here acts as a catalyst which increases the rate of the reaction of acetic acid with hydrogen peroxide to form peroxyacetic acid. The reaction is preferably carried out until the content of peroxyacetic acid has reached more than 90%, and particularly preferably more than 95%, of the content present in the chemical equilibrium.

In a preferred embodiment of the method according to the invention, the reaction mixture for the reaction of acetic acid with hydrogen peroxide contains 0.1 to 2.0% by weight methanesulphonic acid, particularly preferably 0.5 to 2.0% by weight methanesulphonic acid. Through the use of methanesulphonic acid in this concentration range, firstly, the equilibrium may be largely established in a sufficiently short time, and, secondly, an equilibrium peracetic acid can be obtained which has a low corrosive action on metals and shows low decomposition on contact with metals.

In a further preferred embodiment of the method according to the invention, the reaction mixture for reacting acetic acid with hydrogen peroxide contains 5 to 30% by weight methanesulphonic acid. By using methanesulphonic acid in this concentration range, an equilibrium peracetic acid can be obtained, the metering of which can be controlled for disinfection applications via the electrical conductivity of the diluted solution, and which has considerably less corrosive action on metals compared with an equilibrium peracetic acid which contains amounts of sulphuric acid suitable for the same purpose. Furthermore, in this embodiment, the heat development in the reaction mixture is markedly lower than when a corresponding amount of sulphuric acid is used.

For the method according to the invention, acetic acid can be used in pure form or in the form of an aqueous solution. Preferably, acetic acid in pure form is used. Hydrogen peroxide is preferably used in the form of an aqueous solution having a content of 10 to 85% by weight, particularly preferably 25 to 60% by weight. For the reaction, water can optionally be added to the reaction mixture. Preferably, the aqueous reaction mixture does not contain solvent in addition to water. The amounts of acetic acid, hydrogen peroxide and water in the reaction mixture are selected in such a manner that, after establishing equilibrium, the desired content of peroxyacetic acid and hydrogen peroxide is achieved in the equilibrium peracetic acid. For this purpose, acetic acid and hydrogen peroxide are preferably used in a molar ratio in the range from 0.5 to 10, particularly preferably 0.5 to 5.

In the method according to the invention, methanesulphonic acid is preferably used in pure form or in the form of an aqueous solution, particularly preferably in the form of an aqueous solution containing 1 to 40% by weight water. In a preferred embodiment of the method according to the invention, the reaction mixture is produced by mixing acetic acid, aqueous hydrogen peroxide solution having a content of 25 to 60% by weight hydrogen peroxide, and methanesulphonic acid, wherein the methanesulphonic acid can contain 1 to 40% by weight water.

The sequence in which acetic acid, hydrogen peroxide and methanesulphonic acid are added to the reaction mixture is not critical for the method according to the invention. Preferably, however, acetic acid is charged first and hydrogen peroxide is added, in order to avoid formation of mixtures in which high rates of increase of pressure can occur owing to a self-accelerating decomposition. Methanesulphonic acid is preferably added after mixing acetic acid and hydrogen peroxide or is added to one of the feed materials acetic acid or aqueous hydrogen peroxide solution. Particularly preferably, the methanesulphonic acid is added to the hydrogen peroxide solution.

In the method according to the invention, acetic acid and aqueous hydrogen peroxide solution can be mixed with each other batchwise for preparing the aqueous reaction mixture. Alternatively, acetic acid and aqueous hydrogen peroxide solution can also be mixed continuously, for example via a static mixer. For continuous mixing, the method described in WO 02/26459 can be used. After mixing acetic acid and aqueous hydrogen peroxide solution, the reaction to form equilibrium peracetic acid can proceed in any desired container. Since the reaction has a low heat of reaction, the reaction can proceed without cooling and even adiabatically. In a preferred embodiment, the reaction proceeds after the mixing in a storage container or transport container for equilibrium peracetic acid.

The equilibrium peracetic acid according to the invention obtainable by the method according to the invention comprises peroxyacetic acid, hydrogen peroxide, acetic acid, water and methanesulphonic acid. Peroxyacetic acid, hydrogen peroxide, acetic acid and water are in chemical equilibrium in this case. Preferably, the equilibrium peracetic acid of the invention contains 2 to 24% by weight, particularly preferably 3 to 17% by weight, and in particular 4 to 15% by weight peroxyacetic acid.

In a preferred embodiment, the equilibrium peracetic acid of the invention contains 2 to 12% by weight peroxyacetic acid and 5 to 30% by weight methanesulphonic acid, and the weight ratio of methanesulphonic acid to peroxyacetic acid is in the range from 2 to 5. In this embodiment, the dilution of equilibrium peracetic acid to the use concentration for disinfection applications can be controlled via the electrical conductivity of the dilute solution.

In a further preferred embodiment, the equilibrium peracetic acid of the invention further contains up to 5% by weight of one or more surfactants in addition to peroxyacetic acid, hydrogen peroxide, acetic acid, water and methanesulphonic acid. Suitable surfactants for use in equilibrium peracetic acid are known from the prior art, for example from DE 26 16 049 A1, EP 147 207, WO 93/10088, EP 873 687 and WO 98/37762. Preferred surfactants are anionic surfactants, such as alkylsulphonates, alkylsulphates and alkylbenzenesulphonates, and nonionic surfactants, such as fatty alcohol alkoxylates, fatty acid alkoxylates and tertiary amine oxides having a long-chain alkyl radical. By adding surfactants, equilibrium peracetic acids may be produced which, even after dilution to the use concentration for disinfection applications, spread out on a surface that is to be disinfected and wet it completely. This way it may be ensured that, when the dilute solution is sprayed onto a surface, the surface is treated with peroxyacetic acid without gaps.

The equilibrium peracetic acid of the invention may additionally contain one or more stabilizers which stabilize peroxyacetic acid against a catalytic decomposition by heavy metal ions. Suitable stabilizers for peroxyacetic acid are known from the prior art, for example from EP 742 206 B1, paragraphs [0016] and [0017]. Preferred stabilizers are 1-hydroxyethane-1,1-diphosphonic acid, aminotrimethylenephosphonic acid, ethylenediaminetetra-(methylenephosphonic acid), dipicolinic acid and alkali metal salts thereof.

The equilibrium peracetic acid of the invention may additionally contain one or more hardness-stabilizing compounds which can complex calcium ions and magnesium ions. Suitable hardness-stabilizing compounds for equilibrium peracetic acid are known from the prior art, for example from EP 945 405 B1, paragraph [0005]. Preferably, a polymer containing carboxyl groups is used as hardness-stabilizing compound. Particular preference is given to polymers from the series (i) polymers produced by oxidative polymerization of acrolein or of acrolein and acrylic acid, (ii) polyacrylic acid, (iii) copolymers of acrylic acid and another unsaturated carboxylic acid, in particular maleic acid, and (iv) polymaleic acid, wherein the median molecular weight Mw of the polymer is in the range from 500 to 25000, in particular 1000 to 15000. In the equilibrium peracetic acid, part of the carboxyl groups of the hardness-stabilizing polymer can be converted into percarboxyl groups.

In a preferred embodiment, the equilibrium peracetic acid of the invention contains less than 1% by weight of additional compounds apart from peroxyacetic acid, hydrogen peroxide, acetic acid, water, methanesulphonic acid, optionally up to 5% by weight surfactants and optionally up to 10% by weight of polymers containing carboxyl groups.

The examples hereinafter illustrate the invention, but without restricting the subject matter of the invention.

EXAMPLES

Examples 1 to 5

Rate of Establishing Equilibrium for a 15% by Weight Equilibrium Peracetic Acid

A mixture of 28.2% by weight hydrogen peroxide, 28.4% by weight acetic acid, the catalyst in the weight fraction given in Table 1 and water in the remainder was kept at 20° C. and the increase in the content of peroxyacetic acid with time was followed by redox titration until the content of peroxyacetic acid remained constant, i.e. equilibrium had been achieved. For this purpose, samples were taken, the hydrogen peroxide present therein was reacted by rapid titration with Ce(IV) sulphate and ferroin indicator, immediately thereafter an excess of potassium iodide was added and the iodine liberated by reaction with peroxyacetic acid was titrated with thiosulphate and starch indicator. The increase in peroxyacetic acid concentration was evaluated by pseudo-first order kinetics. For this purpose, for the measured values of the first 8 h, $\ln [(c_G-c)/c_G]$ was plotted against the reaction time t, wherein $c_G$ is the peroxyacetic acid concentration in the equilibrium and c is the peroxyacetic acid concentration at time t. The plot gives a straight line, from the gradient of which the times $t_{88}$ for reaching 88% of equilibrium concentration summarized in Table 1 were calculated. This evaluation by pseudo-first order kinetics underestimates the time period for achieving 88% of equilibrium concentration by a factor of about 1.3.

TABLE 1

| Rate of establishing equilibrium | | |
|---|---|---|
| Example | Catalyst | $t_{88}$ in h |
| 1* | 1.0% by weight $H_2SO_4$ | 18 |
| 2* | 2.0% by weight polyphosphoric acid | 16 |
| 3 | 0.5% by weight $CH_3SO_3H$ | 38 |
| 4 | 1.0% by weight $CH_3SO_3H$ | 20 |
| 5 | 1.5% by weight $CH_3SO_3H$ | 14 |

*not according to the invention

Example 6

Storage Stability on Contact with Stainless Steel

A mixture of 1275.5 g of 49.4% by weight hydrogen peroxide PERSYNTH® 500LC, 1171.2 g of acetic acid, 530.2 g of demineralized water, 21.0 g of methanesulphonic acid, 2.0 g of 1-hydroxyethane-1,1-diphosphonic acid and 0.3 g of pyridine-2,6-dicarboxylic acid was reacted to form equilibrium peracetic acid by being allowed to stand at room temperature. The equilibrium peracetic acid formed contained 15.2% by weight peroxyacetic acid, 14.3% by weight hydrogen peroxide and 0.7% by weight methanesulphonic acid. For this equilibrium peracetic acid, a self-accelerating decomposition temperature (SADT) of 50° C. for storage in a non-insulated 17.5 m³ stainless steel tank was determined by an adiabatic warm-storage test in a 1 l spherical Dewar vessel with addition of a pickled metal coupon, using the UN H.2 test method for hazardous materials of UN class 5.2.

Example 7

Storage Stability at a High Content of Methanesulphonic Acid

For an equilibrium peracetic acid containing 5.3% by weight peroxyacetic acid, 23.7% by weight hydrogen peroxide, 4.8% by weight acetic acid, 15.0% by weight methanesulphonic acid, 0.04% by weight 1-hydroxyethane-1,1-diphosphonic acid, 0.01% by weight pyridine-2,6-dicarboxylic acid and 51.1% by weight water, a self-accelerating decomposition temperature (SADT) of at least 60° C. for storage in a 50 kg container was determined by an isoperibolic warm-storage test at 55° C. in a 0.5 l cylindrical Dewar vessel, using the UN H.4 test method for hazardous materials of UN class 5.2.

For the same equilibrium peracetic acid, using the UN H.2 test method for hazardous materials of UN class 5.2 a self-accelerating decomposition temperature (SADT) of 70° C. for storage in a 1 m³ HDPE-IBC was determined in a superadiabatic storage test using 1 l of sample and two HDPE platelets of dimensions 20×60×2 mm in a spherical 1 l Dewar vessel.

For an equilibrium peracetic acid of the same composition, the tests corresponding to section 20, flow diagram of FIG. 20.1 of the UN Recommendations on the Transport of Dangerous Goods, Manual of Tests and Criteria, were carried out and a classification as organic peroxide type F was obtained, i.e. transport in IBCs or tank containers is possible for the equilibrium peracetic acid.

Examples 8 to 11

Corrosive Action of Dilute Solutions and Long-Term Storage Stability

In Example 8, 1141.0 g of 49.4% by weight hydrogen peroxide PERSYNTH® 500LC, 567.6 g of acetic acid, 269.9 g of demineralized water, 19.8 g of 98% by weight sulphuric acid, 1.6 g of 1-hydroxyethane-1,1-diphosphonic acid and 0.24 g of pyridine-2,6-dicarboxylic acid were mixed and reacted to form equilibrium peracetic acid by allowing it to stand at room temperature. The equilibrium peracetic acid formed contained 14.5% by weight peroxyacetic acid, 21.4% by weight hydrogen peroxide and 1.0% by weight sulphuric acid. 3 parts of the equilibrium peracetic acid were diluted with 997 parts of demineralized water to give a disinfectant solution. The resulting disinfectant solution was stored at room temperature in contact with a material coupon (steel material number 1.0038 having the dimensions 60×20×3 mm) which had been pickled in advance for 1 h at 20° C. with inhibited hydrochloric acid. After 24 h, the material coupon had become markedly rusty and the solution stained yellowish, the content of peroxyacetic acid had fallen to 2 ppm (determined using Merck Reflectoquant® test sticks). From the decrease in weight of the material coupon, a material erosion of 0.4 mm/a was calculated. Without a material coupon, the content of peroxyacetic acid after 24 h was 380 ppm, and after 72 h was 370 ppm (determined colorimetrically using ABTS colour reagent).

In Example 9, Example 8 was repeated, but instead of sulphuric acid, 28.6 g of 70% by weight methanesulphonic acid Lutropur MSA from BASF were used, and the amount of demineralized water was decreased to 261.2 g. The equilibrium peracetic acid formed contained 14.6% by weight peroxyacetic acid, 21.6% by weight hydrogen peroxide and 1.0% by weight methanesulphonic acid. The disinfectant solution produced by dilution did not exhibit staining during storage in contact with the material coupon, and also no change was visible on the material coupon after 72 h. From the decrease in weight of the material coupon, a material erosion of less than 0.01 mm/a was calculated. The content of peroxyacetic acid was 380 ppm after 24 h and 350 ppm after 72 h when in contact with the material coupon, and was 380 ppm after 24 h and 360 ppm after 72 h without material coupon.

In Example 10, 1052.7 g of 49.4% by weight hydrogen peroxide PERSYNTH® 500LC, 160.1 g of acetic acid, 479.7 g of demineralized water, 306.2 g of 98% by weight sulphuric acid, 1.4 g of 11-hydroxyethane-1,1-diphosphonic acid and 0.18 g of pyridine-2,6-dicarboxylic acid were mixed and reacted to form equilibrium peracetic acid by allowing it to stand at room temperature. The equilibrium peracetic acid formed contained 5.0% by weight peroxyacetic acid, 23.7% by weight hydrogen peroxide and 15.0% by weight sulphuric acid. 1 part of the equilibrium peracetic acid was diluted with 99 parts of demineralized water to give a disinfectant solution. The resulting disinfectant solution was stored in contact with a material coupon as in Example 8. Already after 15 min, the material coupon was markedly rusty, and after 24 h the solution was stained yellow and turbid and the content of peroxyacetic acid had fallen to 7 ppm (determined using Merck Reflectoquant® test sticks). From the decrease in weight of the material coupon, a material erosion of 8 mm/a was calculated. Without material coupon, the content of peroxyacetic acid after 24 h was 370 ppm (determined colorimetrically using ABTS colour reagent).

In Example 11, Example 10 was repeated, but instead of sulphuric acid, 428.7 g of 70% by weight methanesulphonic acid Lutropur MSA from BASF were used and the amount of demineralized water was decreased to 357.3 g. The equilibrium peracetic acid formed contained 4.7% by weight peroxyacetic acid, 23.9% by weight hydrogen peroxide and 15.0% by weight methanesulphonic acid. The disinfectant solution produced by dilution did not display any staining or turbidity after 48 h of storage in contact with the material coupon, and also on the material coupon no change was visible after 48 h. From the decrease in weight of the material coupon, a material erosion of 2.7 mm/a was calculated. The content of peroxyacetic acid was 270 ppm after 24 h and 80 ppm after 48 h when in contact with the material coupon, and was 360 ppm after 24 h and 300 ppm after 48 h without material coupon.

In addition, storage stability for storage at room temperature over a period of 86 weeks was determined for the undiluted equilibrium peracetic acids, in that in each case samples were taken and the contents of peracetic acid (PAA) and hydrogen peroxide were determined as in Examples 1 to 5. From the peracetic acid (PAA) and hydrogen peroxide contents determined in this way, the total content of active oxygen (AO content) was calculated. The results are compiled in Table 2.

TABLE 2

Long-term storage stability

| Example | Storage period [weeks] | PAA content [% by wt.] | $H_2O_2$ content [% by wt.] | AO content [% by wt.] |
|---|---|---|---|---|
| 8* | 1 | 14.6 | 21.6 | 13.2 |
|  | 3 | 14.6 | 21.6 | 13.2 |
|  | 7 | 14.6 | 21.6 | 13.2 |
|  | 16 | 14.6 | 21.6 | 13.2 |
|  | 26 | 14.5 | 21.4 | 13.1 |
|  | 86 | 12.8 | 20.2 | 12.2 |
| 9 | 1 | 14.6 | 21.6 | 13.2 |
|  | 3 | 14.6 | 21.6 | 13.2 |
|  | 7 | 14.6 | 21.6 | 13.2 |
|  | 16 | 14.6 | 21.6 | 13.2 |
|  | 26 | 14.5 | 21.5 | 13.2 |
|  | 86 | 13.6 | 20.9 | 12.7 |
| 10* | 1 | 5.1 | 23.7 | 12.2 |
|  | 3 | 5.0 | 23.6 | 12.1 |
|  | 7 | 5.0 | 23.6 | 12.1 |
|  | 16 | 4.9 | 2.3 | 12.0 |
|  | 26 | 4.9 | 23.1 | 11.9 |
|  | 86 | 3.9 | 21.6 | 11.0 |
| 11 | 1 | 4.7 | 23.9 | 12.2 |
|  | 3 | 4.7 | 23.9 | 12.2 |
|  | 7 | 4.7 | 23.9 | 12.2 |
|  | 16 | 4.7 | 23.8 | 12.1 |
|  | 26 | 4.7 | 23.9 | 12.2 |
|  | 86 | 4.3 | 24.0 | 12.2 |

*Not according to the invention

The examples show that the equilibrium peracetic acids according to the invention have lower corrosivity and better storage stability than comparable equilibrium peracetic acids which contain sulphuric acid instead of methanesulphonic acid.

For the equilibrium peracetic acids obtained in Examples 10 and 11, in addition, the electrical conductivity was determined at 25° C. undiluted, and after dilution with demineralized water by the factors 10, 100 and 1000, using a WTW 340i Conductometer with Tetracon 325 electrode. The results are summarized in Table 3.

TABLE 3

Electrical conductivity

| Electrical conductivity in mS/cm: | Example | |
|---|---|---|
|  | 10* | 11 |
| undiluted | 300 | 200 |
| 10-fold diluted | 65 | 53 |
| 100-fold diluted | 8.5 | 5.8 |
| 1000-fold diluted | 1.25 | 0.74 |

*not according to the invention

The invention claimed is:

1. A method for producing equilibrium peracetic acid by reacting acetic acid with an aqueous hydrogen peroxide solution, having a content of 25 to 60% by weight hydrogen peroxide, in an aqueous reaction mixture, wherein the reaction is carried out in the presence of methanesulphonic acid as catalyst.

2. The method of claim 1, wherein the reaction mixture contains 0.1 to 2.0% by weight methanesulphonic acid.

3. The method of claim 1, wherein the reaction mixture does not contain additional solvent.

4. The method of claim 1, wherein the reaction mixture is produced by mixing acetic acid, aqueous hydrogen peroxide solution having a content of 25 to 60% by weight hydrogen peroxide, and methanesulphonic acid containing 1 to 40% by weight water.

5. The method of claim 1, wherein acetic acid and hydrogen peroxide are used in a molar ratio in the range from 0.5 to 10.

6. The method of claim 1, wherein the reaction is carried out until the content of peroxyacetic acid has reached more than 90% of the content present in the chemical equilibrium.

7. An equilibrium peracetic acid comprising 2 to 24% by weight peroxyacetic acid, hydrogen peroxide, acetic acid, water and methanesulphonic acid, said equilibrium peracetic acetic being less corrosive than an equilibrium peracetic acid comprising sulfuric acid instead of methanesulphonic acid.

8. The equilibrium peracetic acid of claim 7, further comprising 0 to 5% by weight surfactants, 0 to 10% by weight polymers containing carboxyl groups, and less than 1% by weight additional compounds.

9. The equilibrium peracetic acid of claim 7, comprising from 3 to 17% by weight peroxyacetic acid.

10. The equilibrium peracetic acid of claim 7, comprising from 2 to 12% by weight peroxyacetic acid and from 5 to 30% by weight methanesulphonic acid, and having a weight ratio of methanesulphonic acid to peroxyacetic acid of from 2 to 5.

\* \* \* \* \*